United States Patent
Karl

(10) Patent No.: US 10,731,191 B2
(45) Date of Patent: Aug. 4, 2020

(54) USING DISSOLVED OXYGEN TO INHIBIT LACTIC ACID PRODUCTION DURING PROPAGATION OF YEAST AND/OR HYDROLYSIS OF LIGNOCELLULOSIC BIOMASS

(71) Applicant: POET Research, Inc., Sioux Falls, SD (US)

(72) Inventor: Zachary J Karl, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 15/778,567

(22) PCT Filed: Nov. 10, 2016

(86) PCT No.: PCT/US2016/061336
§ 371 (c)(1),
(2) Date: May 23, 2018

(87) PCT Pub. No.: WO2017/091361
PCT Pub. Date: Jun. 1, 2017

(65) Prior Publication Data
US 2019/0002940 A1    Jan. 3, 2019

Related U.S. Application Data

(60) Provisional application No. 62/259,552, filed on Nov. 24, 2015.

(51) Int. Cl.
| | |
|---|---|
| *C12P 19/14* | (2006.01) |
| *C12P 19/02* | (2006.01) |
| *C12M 1/34* | (2006.01) |
| *C12P 7/10* | (2006.01) |
| *C12M 1/00* | (2006.01) |
| *C12N 1/16* | (2006.01) |
| *C13K 1/02* | (2006.01) |

(52) U.S. Cl.
CPC .............. *C12P 19/14* (2013.01); *C12M 41/34* (2013.01); *C12M 45/09* (2013.01); *C12N 1/16* (2013.01); *C12P 7/10* (2013.01); *C12P 19/02* (2013.01); *C13K 1/02* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 8,450,094 B1 | 5/2013 | Narendranath et al. | |
| 8,815,552 B2 | 8/2014 | Narendranath et al. | |
| 9,034,620 B2 | 5/2015 | Narendranath | |
| 9,034,631 B2 | 5/2015 | Narendranath et al. | |
| 9,234,167 B2 * | 1/2016 | Narendranath | C12P 7/06 |
| 9,340,767 B2 | 5/2016 | Narendranath | |
| 9,416,376 B2 | 8/2016 | Narendranath et al. | |
| 9,663,807 B2 | 5/2017 | Narendranath et al. | |
| 2013/0065289 A1 | 3/2013 | Carlson | |
| 2014/0065700 A1 | 3/2014 | Narendranath et al. | |
| 2014/0209092 A1 | 7/2014 | McDonald et al. | |
| 2015/0072390 A1 | 3/2015 | Narendranath et al. | |
| 2015/0368679 A1 | 12/2015 | Narendranath et al. | |

FOREIGN PATENT DOCUMENTS

| | | | | |
|---|---|---|---|---|
| WO | 2010103530 A1 | | 9/2010 | |
| WO | WO-2010103530 A1 * | | 9/2010 | C12P 7/10 |
| WO | 2011159915 A1 | | 12/2011 | |
| WO | 2016205596 A1 | | 12/2016 | |
| WO | 2017218380 A1 | | 12/2017 | |

OTHER PUBLICATIONS

Ge, X.-Y. et al J Microbiol Biotechnol 2015 vol. 25 pp. 81-88.*
Condon, S. FEMS Microbiol. Rev. 1987 vol. 46, pp. 269-280.*
www.engineeringtoolbox.com/oxygen-solubility-water-d_841.html downloaded Nov. 26, 2019.*
Search report and Written Opinion thereof for International Application No. PCT/US2016/061336, dated Mar. 27, 2017 (20 pages).
Albers et al, "Selective suppression of bacterial contaminants by process conditions during lignocellulose based yeast fermentations", Biotechnology for Biofuels, BioMed Central Ltd, GB, vol. 4:59, Dec. 20, 2011, (pp. 1-8).
Blickstad et al, "Growth and end-product formation in fermenter cultures of Brochothrix thermosphacta ATCC 11509T and two psychrotrophic *Lactobacillus* spp. in different gaseous atmospheres", Journal of Applied Bacteriology, vol. 57, No. 2, 1984, (pp. 213-220).
Condon, Seamus, "Responses of lactic acid bacteria to oxygen", FEMS Microbiology Reviews, vol. 46, No. 3, 1987, (pp. 269-280).
Ge et al, "Regulation of Metabolic Flux in Lactobacillus casei for Lactic Acid Production by Overexpressed IdhL Gene with Two-Stage Oxygen Supply Strategy", Journal of Microbiology and Biotechnology, vol. 25, No. 1, Jan. 2015, (pp. 81-88).

* cited by examiner

*Primary Examiner* — Heidi Reese
(74) *Attorney, Agent, or Firm* — Kagan Binder, PLLC

(57) ABSTRACT

Embodiments of the present disclosure involve systems and methods that inhibit the production of lactic acid during propagation of yeast and/or during hydrolysis of cellulose by including a sufficient amount of dissolved oxygen.

18 Claims, 3 Drawing Sheets

USING DISSOLVED OXYGEN TO INHIBIT LACTIC ACID PRODUCTION DURING PROPAGATION OF YEAST AND/OR HYDROLYSIS OF LIGNOCELLULOSIC BIOMASS

RELATED APPLICATION

The present patent application claims the benefit of commonly owned provisional Application having Ser. No. 62/259,552, filed on Nov. 24, 2015, which provisional Application is incorporated herein by reference in its entirety.

BACKGROUND

The present disclosure is related to systems and methods for propagating yeast and/or hydrolyzing lignocellulosic material into one or more monosaccharides that can be converted into one or more biochemicals by one or more types of organisms (e.g., yeast).

SUMMARY

Embodiments of the present disclosure include a method of treating lignocellulosic biomass, wherein the method includes converting cellulose in the lignocellulosic biomass into an oligosaccharide and/or a monosaccharide in the presence of an amount of oxygen that inhibits the production of lactic acid by a bacteria.

Embodiments of the present disclosure also include a system for treating cellulose in lignocellulosic biomass, wherein the system includes:

a) an enzymatic hydrolysis system comprising one or more vessels containing an aqueous slurry, wherein the aqueous slurry comprises the lignocellulosic biomass that comprises the cellulose and one or more enzymes that can convert the cellulose into an oligosaccharide and/or a monosaccharide, wherein the enzymatic hydrolysis system is configured to convert cellulose in the lignocellulosic biomass into the oligosaccharide and/or the monosaccharide in the presence of an amount of oxygen that inhibits the production of lactic acid by a bacteria; and b) a source of gas in fluid communication with the enzymatic hydrolysis system, wherein the source of gas is configured to add the gas to the enzymatic hydrolysis system so that aqueous slurry comprises dissolved oxygen in an amount that inhibits the production of lactic acid by a bacteria, wherein the gas comprises oxygen.

Embodiments of the present disclosure include a method of propagating yeast that can convert one or more monosaccharides into a biochemical, the method including:

a) providing a first cell mass of the yeast in an aqueous propagation medium; and b) propagating the first cell mass of the yeast in the aqueous propagation medium in the presence of an amount of oxygen that inhibits the production of lactic acid by a bacteria and for a time period to form a second cell mass of the yeast that is greater than the first cell mass of the yeast, wherein lactic acid is present in the aqueous propagation medium during the time period in an amount from 0 to 150 milligrams lactic acid per liter of aqueous propagation medium.

Embodiments of the present disclosure also include a system for propagating yeast that includes:

a) a yeast propagation reactor vessel including:
i) an aqueous propagation medium; and
ii) a first cell mass of the yeast, wherein the yeast propagation reactor is configured so that the first cell mass of the yeast can grow for a time period to form a second cell mass of the yeast that is greater than the first cell mass of yeast; and b) a source of a gas coupled to the propagation reactor vessel to incorporate an amount of the gas into the aqueous propagation medium so that the aqueous propagation medium includes dissolved oxygen in an amount that inhibits the production of lactic acid by a bacteria, wherein the gas includes oxygen, and wherein lactic acid is present in the aqueous propagation medium during the time period in an amount from 0 to 150 milligrams lactic acid per liter of aqueous propagation medium.

DETAILED DESCRIPTION

Figure 1:
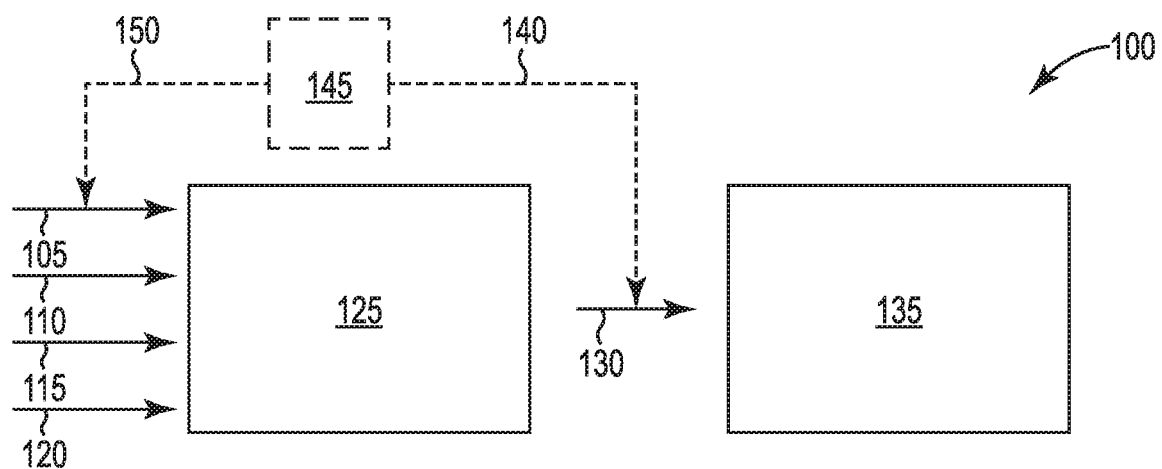
FIG. 1 shows a schematic illustration of an embodiment of a system according to the present disclosure.

Embodiments of the present disclosure include a method of treating lignocellulosic biomass that includes converting cellulose in the lignocellulosic biomass into an oligosaccharide and/or a monosaccharide in the presence of an amount of oxygen (i.e., diatomic oxygen) that inhibits the production of lactic acid by a bacteria.

Lactic acid can be produced upstream of fermentation in a cellulosic process for converting one or more types of monosaccharides into a biochemical. For example, when cellulose is converted into oligosaccharides and/or monosaccharides (e.g., glucose) bacteria within the genus of *Lactobacillus* can produce lactic acid under certain conditions. Unfortunately, lactic acid can inhibit yeast in fermentation, which can be downstream from converting cellulose into oligosaccharides and monosaccharides. While not being bound by theory, it is believed that oxygen can inhibit lactic acid production. Advantageously, because lactic acid production can be controlled with oxygen instead of other parameters (e.g., temperature and/or pH), conditions such as temperature and/or pH for converting cellulose into glucose can be set so that enzymes perform as desired. For example, pH and temperature can be at optimum for enzymes. If desired, pH and/or temperature do not need to be adjusted to inhibit lactic acid producing bacteria.

As discussed in further detail below, embodiments of the present disclosure include converting cellulose in the lignocellulosic biomass into an oligosaccharide and/or a monosaccharide by providing an aqueous slurry that includes the lignocellulosic biomass that includes the cellulose; one or more enzymes that can convert the cellulose into the oligosaccharide and/or the monosaccharide; and dissolved oxygen in an amount that inhibits the production of lactic acid by a bacteria.

Exemplary lignocellulosic biomass includes switchgrass and agricultural residue (e.g., corn cobs and corn stover (i.e., corn stalks and leaves)).

Enzymes that can convert the cellulose into the oligosaccharide and/or the monosaccharide are also referred to as cellulases. As mentioned, one or more types of cellulases can be used to enzymatically hydrolyze cellulose into a monosaccharide such as glucose so that the glucose can be used downstream in fermentation.

Oxygen can be included in an aqueous slurry as described herein so that dissolved oxygen is present in an amount that inhibits the production of lactic acid by a bacteria. While not being bound by theory, it is believed that there may be one or more mechanisms during hydrolysis of cellulose that compete for oxygen. For example, some enzymes utilize oxygen to convert cellulose to glucose. Such enzymes are described in PCT publications WO 2014/072392 and WO 2014/130812. As another example, lignin degradation can generate free radicals that may also consume oxygen. Accordingly, an amount of oxygen may be supplied to account for any oxygen consumption by such competing processes and still provide a sufficient amount of dissolved oxygen that inhibits the production of lactic acid by a bacteria.

In some embodiments, dissolved oxygen is present in an aqueous slurry in an amount of at least 11 milligrams of dissolved oxygen per liter of slurry, at least 15 milligrams of dissolved oxygen per liter of slurry, or even at least 30 milligrams of dissolved oxygen per liter of slurry. In some embodiments, dissolved oxygen is present in an aqueous slurry in an amount in the range from 11 to 200 milligrams of dissolved oxygen per liter of slurry, or even in the range from 11 to 50 milligrams of dissolved oxygen per liter of slurry. As used herein, a "slurry" in enzymatic hydrolysis includes a liquid fraction and a solids fraction. In some embodiments, a slurry can include solids in an amount of less than 50% by weight of the total slurry (e.g., between 10-20% by weight of the total slurry) and liquid in an amount of 50% or more by weight of the total slurry). As mentioned below, during enzymatic hydrolysis the slurry can be at a temperature between 50'C to 60° C. As the solubility of oxygen in the slurry changes with temperature, the amount of oxygen added to the slurry can be adjusted so that the amount of dissolved oxygen in the slurry is at least 11 milligrams of dissolved oxygen per liter of slurry.

Dissolved oxygen can be present in an aqueous slurry by adding a gas to the aqueous slurry. One or more techniques can be used to introduce a gas into the aqueous slurry. For example, a gas can be introduced into the headspace of hydrolysis reactor so that the gas diffuses into the aqueous slurry. As another example, a gas can be sparged into the aqueous slurry so that the gas bubbles up and through the aqueous slurry and oxygen transfers into the aqueous slurry.

Optionally, the aqueous slurry can be agitated or mixed to facilitate transferring oxygen into and throughout the aqueous slurry so as to achieve the desired dissolved oxygen levels. For example, a continuous stirred tank reactor (CSTR) can be used to agitate or mix the aqueous slurry. The speed of the stirring mechanism (rpms) can be adjusted based on a variety of factors such as tank size, slurry viscosity, and the like.

One or more gases can be supplied to or used to form an aqueous slurry so that the aqueous slurry has a sufficient amount of dissolved oxygen to inhibit the production of lactic acid by a bacteria. Examples of such gases include pure oxygen gas or a gas mixture that includes oxygen such as air.

An oxygen-containing gas can be supplied to an aqueous slurry during hydrolysis according to a variety of timing protocols. For example, an oxygen-containing gas can be supplied continuously during hydrolysis (e.g., liquefaction and saccharification) or at one or more partial time periods throughout hydrolysis (e.g., only liquefaction or saccharification, or a portion of each thereof). It is noted that oxygen may be consumed in larger amounts at the beginning of a hydrolysis process due to, e.g., relatively high enzymatic action, relatively high lignin degradation, combinations of these, and the like. In some embodiments, a relatively higher amount of an oxygen-containing gas can be supplied during a first part of enzymatic hydrolysis. For example, an oxygen-containing gas can be supplied from when enzyme is combined with an aqueous slurry until at least the through liquefaction.

FIG. 1 shows a schematic illustration of an embodiment of a system 100 according to the present disclosure.

As shown in FIG. 1, system 100 includes an enzymatic hydrolysis system 125 that includes one or more vessels (not shown) containing an aqueous slurry. The aqueous slurry includes lignocellulosic biomass 110 that includes cellulose and one or more enzymes 115 that can convert the cellulose into an oligosaccharide and/or a monosaccharide. The aqueous slurry also includes an aqueous liquid 120. The enzymatic hydrolysis system 125 is configured to convert cellulose in the lignocellulosic biomass into the oligosaccharide and/or the monosaccharide in the presence of an amount of oxygen that inhibits the production of lactic acid by a bacteria. As shown, the aqueous slurry can be formed by combining the lignocellulosic biomass 110 that comprises the cellulose, and one or more enzymes 115 that can convert the cellulose into the oligosaccharide and/or the monosaccharide. If a sufficient amount of aqueous liquid is not present with the biomass 110 and/or enzymes 115, aqueous liquid 120 can be combined with the biomass 110 and enzymes 115. A source of gas 105 can be in fluid communication with an enzymatic hydrolysis system 125 and configured to add the gas to the enzymatic hydrolysis system 125 so that an aqueous slurry includes dissolved oxygen in an amount that inhibits the production of lactic acid by a bacteria.

While in the hydrolysis system 125, the aqueous slurry can be maintained at a pH and temperature for a time period to convert at least a portion of the cellulose in the lignocellulosic biomass into an oligosaccharide and/or a monosaccharide in the presence of an amount of oxygen that inhibits the production of lactic acid by a bacteria.

Optionally, as shown by the dashed lines in FIG. 1, the amount of oxygen delivered to the hydrolysis system 125 can be controlled by measuring the amount, if any, of lactic acid in aqueous slurry 130. The measured amount of lactic acid 140 can be processed by a controller 145 to determine the amount 150 of an oxygen-containing gas that should be added to the aqueous slurry in hydrolysis system 125 from source 105.

In some embodiments, the amount of acceptable measured lactic acid in aqueous slurry 130 is from 0 to 150 milligrams of lactic acid per liter of slurry, or even from 0 to 100 milligrams of lactic acid per liter of slurry. In some embodiments, an amount of dissolved oxygen that can inhibit the production of lactic acid so that it is less than 150 milligrams of lactic acid per liter of slurry includes at least 11 milligrams of dissolved oxygen per liter of slurry.

As shown in FIG. 1, the aqueous slurry 130 includes a monosaccharide such as glucose and can be combined with yeast in fermentation system 135 so that the yeast converts the monosaccharide into a biochemical. In some embodiments, the biochemical includes ethanol.

Figure 2:
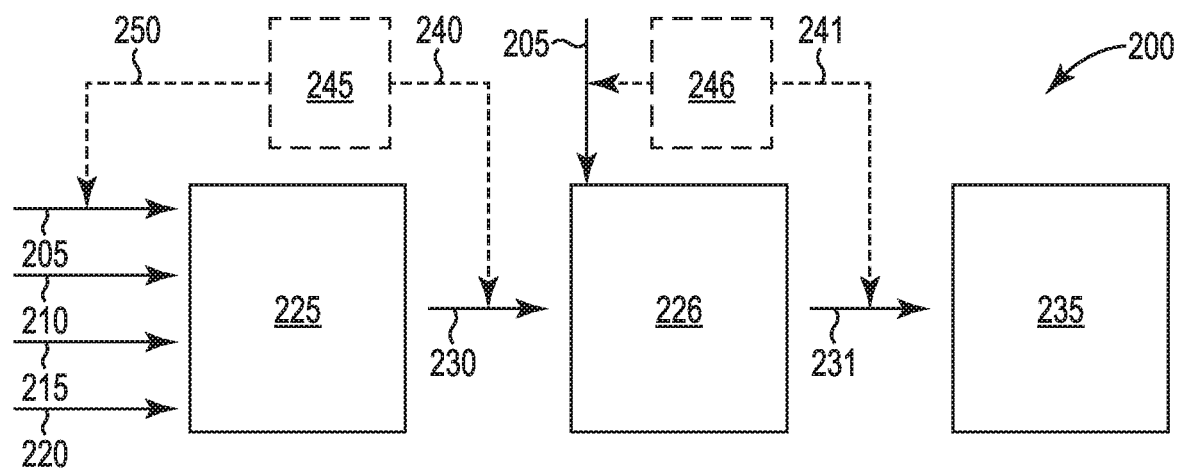
FIG. 2 shows a schematic illustration of another embodiment of a system according to the present disclosure.

FIG. 2 shows a schematic illustration of an embodiment of a system 200 according to the present disclosure.

As shown in FIG. 2, system 200 includes an enzymatic hydrolysis system that includes a first enzymatic hydrolysis system (also referred to as a "liquefaction system") 225 and a second enzymatic hydrolysis system (also referred to as a "saccharification system") 226. The liquefaction system 225 includes one or more vessels (not shown) containing a first aqueous slurry. The first aqueous slurry includes lignocellulosic biomass 210 that includes cellulose and one or more enzymes 215 that can convert the cellulose into an oligosaccharide and/or a monosaccharide. The aqueous slurry also includes an aqueous liquid 220. The liquefaction system 225 is configured to maintain the first aqueous slurry at a pH and temperature for a time period to convert at least a portion of the cellulose in the lignocellulosic biomass into an oligosaccharide and/or a monosaccharide, and form a second aqueous slurry 230. In some embodiments, the temperature of the first aqueous slurry is in a range from 45° C. to 65° C., or even from 50° C. to 60° C. In some embodiments, the pH of the first aqueous slurry is in a range from 4 to 6, or even from 4.5 to 5.5. In some embodiment, the liquefaction time period is in the range from 2 to 20 hours, or even from 6 to 8 hours. As shown, the first aqueous slurry can be formed by combining the lignocellulosic biomass that comprises the cellulose, and one or more enzymes that can convert the cellulose into the oligosaccharide and/or the monosaccharide. If a sufficient amount of aqueous liquid is not present with the biomass 210 and/or enzymes 215, aqueous liquid 220 can be combined with the biomass 210 and enzymes 215. A source of gas 205 can be in fluid communication with the liquefaction system 225 and configured to add the gas to the liquefaction system 225 so that the first aqueous slurry includes dissolved oxygen in an amount that inhibits the production of lactic acid by a bacteria.

Optionally, as shown by the dashed lines in FIG. 2, the amount of oxygen delivered to the liquefaction system 225 can be controlled by measuring the amount, if any, of lactic acid in second aqueous slurry 230. The measured amount of lactic acid 240 can be processed by a controller 245 to determine the amount 250 of an oxygen-containing gas that should be added to the aqueous slurry in liquefaction system 225 from source 205.

In some embodiments, the amount of acceptable lactic acid in second aqueous slurry 230 is from 0 to 150 milligrams of lactic acid per liter of slurry, or even from 0 to 100 milligrams of lactic acid per liter of slurry. In some embodiments, an amount of dissolved oxygen that can inhibit the production of lactic acid so that it is less than 150 milligrams of lactic acid per liter of slurry includes at least 1 milligrams of dissolved oxygen per liter of slurry.

As shown in FIG. 2, a saccharification system 226 including one or more batch reactors (not shown) is in fluid communication with the liquefaction system 225 to receive the second aqueous slurry 230. The saccharification system 226 is configured to maintain the second aqueous slurry at a pH and temperature for a time period to convert at least a portion of the cellulose in the lignocellulosic biomass into an oligosaccharide and/or a monosaccharide, and form a third aqueous slurry 231. In some embodiments, the temperature of the second aqueous slurry is in a range from 45° C. to 65° C., or even from 50° C. to 60° C. In some embodiments, the pH of the second aqueous slurry is in a range from 4 to 6, or even from 4.5 to 5.5. In some embodiment, the saccharification time period is in the range from 48 to 120 hours, or even from 112 to 114 hours. A source of gas 205 can be in fluid communication with the saccharification system 226 and configured to add the gas to the saccharification system 226 so that the second aqueous slurry in saccharification system 226 includes dissolved oxygen in an amount that inhibits the production of lactic acid by a bacteria.

Optionally, as shown by the dashed lines in FIG. 2, the amount of oxygen delivered to the saccharification system 226 can be controlled by measuring the amount, if any, of lactic acid in second aqueous slurry 231. The measured amount of lactic acid 241 can be processed by a controller 246 to determine the amount 251 of an oxygen-containing gas that should be added to the aqueous slurry in saccharification system 226 from source 205.

In some embodiments, the amount of acceptable lactic acid in aqueous slurry 231 is from 0 to 150 milligrams of lactic acid per liter of slurry, or even from 0 to 100 milligrams of lactic acid per liter of slurry. In some embodiments, an amount of dissolved oxygen that can inhibit the production of lactic acid so that it is less than 150 milligrams of lactic acid per liter of slurry includes at least 11 milligrams of dissolved oxygen per liter of slurry.

As shown in FIG. 2, the aqueous slurry 231 includes a monosaccharide such as glucose and can be combined with yeast in fermentation system 235 so that the yeast converts the monosaccharide into a biochemical. In some embodiments, the biochemical includes ethanol.

Embodiments of the present disclosure also include methods of propagating yeast that can convert one or more monosaccharides into a biochemical. The methods include providing a first cell mass of the yeast in an aqueous propagation medium, and propagating the first cell mass of the yeast in the aqueous propagation medium in the presence of an amount of oxygen that inhibits the production of lactic acid by a bacteria and for a time period to form a second cell mass of the yeast that is greater than the first cell mass of the yeast. The dissolved oxygen is present in the aqueous propagation medium in an amount of at least 11 milligrams of dissolved oxygen per liter of aqueous propagation medium. In some embodiments, the method includes measuring a sample of the aqueous propagation medium to determine the presence and amount of lactic acid in the aqueous propagation medium; determining an amount of oxygen to add to the aqueous propagation medium based on the amount of lactic acid measured; and adding a gas to the aqueous propagation medium so that the aqueous propagation medium includes dissolved oxygen in an amount that inhibits the production of lactic acid by a bacteria. The gas includes oxygen.

During the propagation time period the lactic acid is present in the aqueous propagation medium in an amount from 0 to 150 milligrams lactic acid per liter of aqueous propagation medium.

The propagation medium can include a carbon source that can support growth of the first cell mass of the yeast. In some embodiments, the carbon source includes xylose and/or glucose.

The propagation medium can also include a nutrient source that can support growth of the first cell mass of the yeast. In some embodiments, the nutrient source includes a stillage component and/or yeast extract.

Embodiments of the present disclosure also include a system for propagating yeast. The system can include a yeast propagation reactor vessel that includes an aqueous propagation medium; and a first cell mass of the yeast. The yeast propagation reactor is configured so that the first cell mass of the yeast can grow for a time period to form a second cell mass of the yeast that is greater than the first cell mass of yeast.

The system can also include a source of a gas coupled to the propagation reactor vessel to incorporate an amount of the gas into the aqueous propagation medium so that the aqueous propagation medium includes dissolved oxygen in an amount that inhibits the production of lactic acid by a bacteria.

Optionally, the system can include an agitation system coupled to the yeast propagation reactor vessel in a manner so that the propagation medium can be agitated or mixed to facilitate transferring oxygen into and throughout the propagation medium so as to achieve the desired dissolved oxygen levels. For example, a continuous stirred tank reactor (CSTR) can be used to agitate or mix the propagation medium. The speed of the stirring mechanism (rpms) can be adjusted based on a variety of factors such as tank size, slurry viscosity, and the like.

Methods and systems for propagating yeast are also described in the following U.S. patent documents: U.S. Pat. No. 8,450,094 (Narendranath et al.); U.S. Pat. No. 9,034,631 (Narendranath et al.); U.S. Pub No. 2014/0065700 (Narendranath et al.); and U.S. Pub No. 2014/0273166 (Narendranath), the entirety of each patent document being incorporated herein by reference.

EXAMPLES

Example 1

Figure 3:
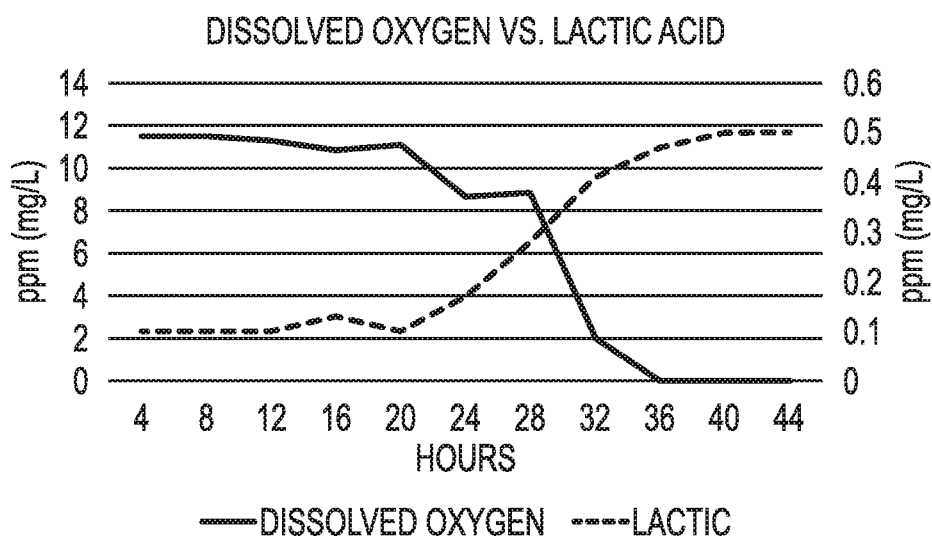
FIG. 3 graphically illustrates lactic acid and dissolved oxygen data from Example 1.

A slurry of corn stover was saccharified in a seed fermenter for 120 hours at 50° C. and a pH of 5. As oxygen levels dropped below 11 ppm during the saccharification, lactic acid levels began to rise. FIG. 3 graphically illustrates lactic acid and dissolved oxygen data gathered from the cellulosic seed fermenter. The data in FIG. 3 indicates a direct trade-off between lactic acid production and dissolved oxygen, where lactic acid production begins as dissolved oxygen levels drop below 11 ppm.

Example 2

Figure 4:
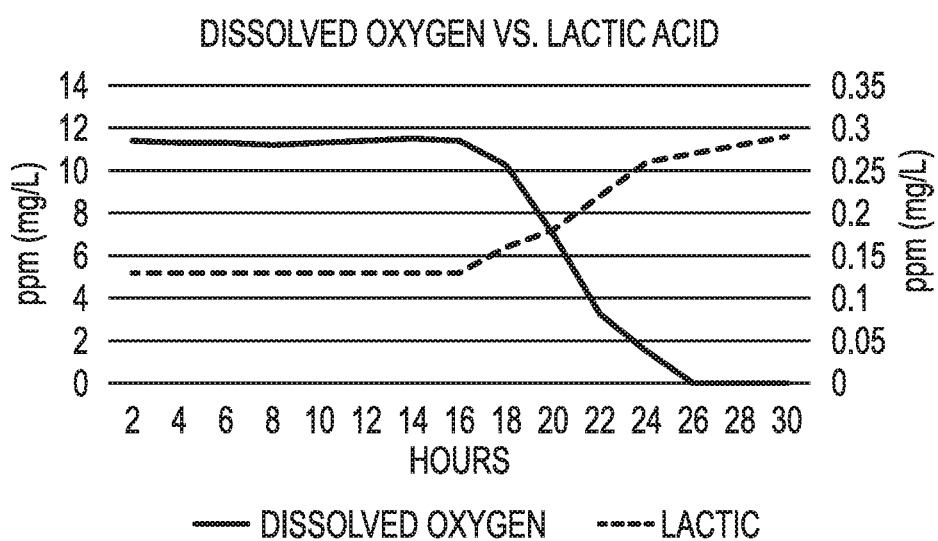
FIG. 4 graphically illustrates lactic acid and dissolved oxygen data from Example 2.

A slurry of corn stover was saccharified in a seed fermenter for 120 hours at 50° C. and a pH of 5. As oxygen levels dropped below 11 ppm during the saccharification, lactic acid levels began to rise. FIG. 4 graphically illustrates lactic acid and dissolved oxygen data gathered from a seed fermenter which was independent from EXAMPLE 1. The data in FIG. 4 directly supports data found EXAMPLE 1, indicating a direct trade-off between lactic acid production and dissolved oxygen where lactic acid production begins as dissolved oxygen levels drop below 11 ppm.

What is claimed is:

1. A method of propagating yeast that can convert one or more monosaccharides into a biochemical, the method comprising:
   a) providing a first cell mass of the yeast in an aqueous propagation medium, wherein the aqueous propagation medium comprises a cellulosic hydrolysate that includes *Lactobacillus* bacteria that can produce lactic acid; and
   b) propagating the first cell mass of the yeast in the aqueous propagation medium in the presence of an amount of dissolved oxygen that inhibits the production of lactic acid by the *Lactobacillus* bacteria and for a time period to form a second cell mass of the yeast that is greater than the first cell mass of the yeast, wherein lactic acid is present in the aqueous propagation medium during the time period in an amount from 0 to 150 milligrams lactic acid per liter of aqueous propagation medium.

2. The method of claim 1, wherein the dissolved oxygen is present in the aqueous propagation medium in an amount of at least 11 milligrams of dissolved oxygen per liter of aqueous propagation medium.

3. The method of claim 1, further comprising
   a) measuring a sample of the aqueous propagation medium to determine the presence and amount of lactic acid in the aqueous propagation medium;
   b) determining an amount of oxygen to add to the aqueous propagation medium based on the amount of lactic acid measured in step (a); and
   c) adding a gas to the aqueous propagation medium so that the aqueous propagation medium comprises dissolved oxygen in an amount that inhibits the production of lactic acid by the *Lactobacillus* bacteria, wherein the gas comprises oxygen.

4. The method of claim 1, wherein lactic acid is present in the aqueous propagation medium during the time period in an amount from 0 to 100 milligrams lactic acid per liter of aqueous propagation medium.

5. The method of claim 1, wherein the dissolved oxygen is present in the aqueous propagation medium in an amount of at least 15 milligrams of dissolved oxygen per liter of aqueous propagation medium.

6. The method of claim 1, wherein the dissolved oxygen is present in the aqueous propagation medium in an amount of at least 30 milligrams of dissolved oxygen per liter of aqueous propagation medium.

7. The method of claim 1, wherein the dissolved oxygen is present in the aqueous propagation medium in an amount from 15 to 200 milligrams of dissolved oxygen per liter of aqueous propagation medium.

8. The method of claim 1, wherein the propagation medium comprises:
   a) a carbon source that can support growth of the first cell mass of the yeast, wherein the carbon source comprises xylose and/or glucose; and
   b) a nutrient source that can support growth of the first cell mass of the yeast, wherein the nutrient source comprises a stillage component and/or yeast extract.

9. The method of claim 3, wherein adding gas comprises introducing the gas into a headspace of a vessel that contains the aqueous propagation medium so that the gas diffuses into the aqueous propagation medium.

10. The method of claim 3, wherein adding gas comprises sparging the gas into the aqueous propagation medium so that the gas transfers into the aqueous propagation medium.

11. The method of claim 3, further comprising exposing the second cell mass of the yeast to anaerobic conditions to convert monosaccharide into a biochemical.

12. The method of claim 11, wherein the second cell mass of yeast is combined with the monosaccharide in a fermentation system to convert monosaccharide into a biochemical under anaerobic conditions.

13. The method of claim 11, wherein the monosaccharide is derived from a method of treating lignocellulosic biomass in an aqueous slurry, wherein the method comprises converting cellulose in the lignocellulosic biomass into the monosaccharide in the presence of an amount of dissolved oxygen that inhibits the production of lactic acid by *Lactobacillus* bacteria, wherein lactic acid is present in an amount from 0 to 150 milligrams lactic acid per liter of aqueous slurry.

14. The method of claim 13, wherein converting cellulose in the lignocellulosic biomass into the monosaccharide comprises providing the aqueous slurry comprising:

a) the lignocellulosic biomass that comprises the cellulose;
b) one or more enzymes that can convert the cellulose into the monosaccharide; and
c) dissolved oxygen in an amount that inhibits the production of lactic acid by the *Lactobacillus* bacteria.

15. The method of claim 13, wherein the dissolved oxygen is present in the aqueous slurry in an amount of at least 11 milligrams of dissolved oxygen per liter of aqueous slurry.

16. The method of claim 13, wherein converting cellulose in the lignocellulosic biomass into the monosaccharide comprises:
   a) providing the aqueous slurry comprising the lignocellulosic biomass that comprises the cellulose and one or more enzymes that can convert the cellulose into the monosaccharide;
   b) adding a gas to the aqueous slurry so that aqueous slurry comprises dissolved oxygen in an amount that inhibits the production of lactic acid by the *Lactobacillus* bacteria, wherein the gas comprises oxygen;
   c) maintaining the aqueous slurry at a pH and temperature for a time period to convert at least a portion of the cellulose in the lignocellulosic biomass into the monosaccharide, wherein the dissolved oxygen inhibits the production of lactic acid by the *Lactobacillus* bacteria.

17. The method of claim 13, wherein converting cellulose in the lignocellulosic biomass into the monosaccharide comprises:
   a) maintaining an aqueous slurry at a pH and temperature for a time period to convert at least a portion of the cellulose in the lignocellulosic biomass into the monosaccharide, wherein the aqueous slurry comprises the lignocellulosic biomass that comprises the cellulose and one or more enzymes that can convert the cellulose into the monosaccharide;
   b) after step (a), measuring a sample of the aqueous slurry to determine the presence and amount of lactic acid in the aqueous slurry;
   c) determining an amount of oxygen to add to the aqueous slurry based on the amount of lactic acid measured in step (b).

18. The method of claim 17, further comprising adding a gas to the aqueous slurry so that the aqueous slurry comprises dissolved oxygen in an amount that inhibits the production of lactic acid by the *Lactobacillus* bacteria, wherein the gas comprises oxygen.

* * * * *